United States Patent [19]
Hoerby

[11] Patent Number: 5,743,885
[45] Date of Patent: Apr. 28, 1998

[54] BANDAGE FOR FIXATING AN ORAL, ENDO-TRACHEAL ANAESTHESIA TUBE RELATIVE TO THE MOUTH OF A PERSON AND AN ASSEMBLY FOR FIXATING AN ORAL, ENDO-TRACHEAL ANAESTHESIA TUBE RELATIVE TO THE MOUTH OF A PERSON

[75] Inventor: John Hoerby, Hellerup, Denmark

[73] Assignee: Nikomed ApSl, Denmark, Sweden

[21] Appl. No.: 669,429

[22] PCT Filed: Jan. 6, 1995

[86] PCT No.: PCT/DK95/00012

§ 371 Date: Sep. 17, 1996

§ 102(e) Date: Sep. 17, 1996

[87] PCT Pub. No.: WO95/18645

PCT Pub. Date: Jul. 13, 1995

[30] Foreign Application Priority Data

Jan. 6, 1994 [DK] Denmark .................. 0004/94

[51] Int. Cl.$^6$ .................................... A61M 5/32
[52] U.S. Cl. .................. 604/180; 604/174; 604/179; 128/DIG. 26
[58] Field of Search .................. 604/174, 179, 604/180; 128/DIG. 26

[56] References Cited

U.S. PATENT DOCUMENTS

| | | | |
|---|---|---|---|
| 3,924,636 | 12/1975 | Addison | 128/351 |
| 3,927,676 | 12/1975 | Schultz | 128/351 |
| 4,142,527 | 3/1979 | Garcia | 604/180 |
| 4,270,529 | 6/1981 | Muto | 128/200.26 |
| 4,326,515 | 4/1982 | Shaffer et al. | 128/207.17 |
| 4,449,527 | 5/1984 | Hinton | 128/207.17 |
| 4,490,141 | 12/1984 | Lacko et al. | 604/180 |
| 4,838,867 | 6/1989 | Kalt et al. | 604/180 |
| 4,844,061 | 7/1989 | Carroll | 604/180 X |
| 4,867,154 | 9/1989 | Potter et al. | 604/180 X |
| 5,038,778 | 8/1991 | Lott | 128/207.17 |
| 5,221,265 | 6/1993 | List | 604/180 |
| 5,546,938 | 8/1996 | McKenzie | 604/180 X |

FOREIGN PATENT DOCUMENTS

| | | |
|---|---|---|
| 0 392 498 | 10/1990 | European Pat. Off. . |
| 32 18 368 | 11/1983 | Germany . |
| 33 10 661 | 11/1983 | Germany . |

*Primary Examiner*—Sam Rimell
*Assistant Examiner*—Robert V. Racunas
*Attorney, Agent, or Firm*—Stephen C. Glazier

[57] ABSTRACT

The invention is a bandage and an assembly especially designed for proper fixation of an oral, endo-tracheal anaesthesia tube relative to the mouth of a person. The bandage includes a support sheet of a flexible, substantially non-ductile material defining opposite side surfaces and defining contiguous first and second parts. The first part is provided with a coating, at one side surface thereof, of a first adhesive exhibiting the ability of adhering to the skin of a person, and being configured so as to allow the first part to be adhered to the cheek of the person leaving the mouth unobstructed. The second part is provided with a coating, at one side surface thereof, of a second adhesive exhibiting the ability of adhering to the endo-tracheal anaesthesia tube, and being configured so as to allow the second part to be adhered to a segment of the tube extending outwardly from the mouth of the person.

57 Claims, 5 Drawing Sheets

BANDAGE FOR FIXATING AN ORAL, ENDO-TRACHEAL ANAESTHESIA TUBE RELATIVE TO THE MOUTH OF A PERSON AND AN ASSEMBLY FOR FIXATING AN ORAL, ENDO-TRACHEAL ANAESTHESIA TUBE RELATIVE TO THE MOUTH OF A PERSON

A bandage for fixating an oral, endo-tracheal anaesthesia tube relative to the mouth of a person and an assembly for fixating an oral, endo-tracheal anaesthesia tube relative to the mouth of a person.

The present invention relates to a bandage for fixating an oral, endo-tracheal anaesthesia tube relative to the mouth of a person and an assembly for fixating an oral, endo-tracheal anaesthesia tube relative to the mouth of a person which assembly comprises a mouth piece and a bandage.

Endo-tracheal anaesthesia tubes have been used for a long time, and oral intubation of the endo-tracheal anaesthesia tube has also been known for a long time. Oral, endo-tracheal anaesthesia tubes, however, have previously mainly been fixated in accordance with two alternative techniques.

According to the first technique, the endo-tracheal anaesthesia tube has been fixated relative to the mouth of a person by means of conventional tape used for medical purposes and supplied in rolls. One or two pieces of tape are in accordance with this technique used for fixating the oral, endo-tracheal anaesthesia tube as a first piece of tape is applied to one cheek of the patient or person and passed or twisted round the oral, endo-tracheal anaesthesia tube and fixated to the same or the opposite cheek. Provided the second piece of tape is used, the second piece of tape is fixated to the opposite cheek and also passed around or twisted around the oral, endo-tracheal anaesthesia tube and fixated to one or the other cheek. Most often, the first and the second piece of tape, if two pieces of tape are used, are positioned in an X-configuration.

According to the second or alternative technique, an especially designed fixation device is used. Examples of endo-tracheal anaesthesia tube holders or fixation devices are described in U.S. Pat. No. 4,449,527, U.S. Pat. No. 4,270,529, German patent DE-PS 32 18 368 and published German patent application No. DE-OS 33 10 661. An example of a combination of the technique of applying tape and employing a fixation structure applied to the head of the patient or person carrying the endo-tracheal anaesthesia tube is described in published European patent application No. EP 0 392 498. Reference is made to the above patents and patent applications and the above U.S. patents are further incorporated in the present specification by reference.

Common to the prior art fixation devices used for fixating an oral, endo-tracheal anaesthesia tube are the severe drawbacks as in the complexity of the devices which are of elaborate structure and consequently extremely costly. Furthermore, since most of the devices require the employment of a strap or wire to be fixated round the neck of the patient or person, problems may arise as to a proper fixation of the oral, endo-tracheal anaesthesia tube which may cause severe damage to the patient or person. Still further, due to the complexity of the devices, the devices are not perfectly applicable in connection with patients or persons which have to carry an endo-tracheal anaesthesia tube for an extended period of time after a medical operation has been completed. It is to be realized that oral, endo-tracheal anaesthesia tubes are frequently used even after the medical operation has been completed and while the patient or person is hospitalized for further treatment or recovery.

An object of the present invention is to provide a bandage especially designed for fixating an oral, endo-tracheal anaesthesia tube and eliminating the above described problems relating to the proper fixation of an oral endo-tracheal anaesthesia tube relative to the mouth of the patient or person and further in relation to the correct position of the endo-tracheal anaesthesia tube within the trachea of the patient or person.

It is a further object of the present invention to provide an especially designed device for the fixating of an oral, endo-tracheal anaesthesia tube implemented as a bandage for adhering to the area round the mouth of the patient or person and to the tube which device implemented as a bandage provides a proper fixation of the oral, endo-tracheal anaesthesia tube and is highly convenient to carry and further easily applicable and still further allows a refixation of the bandage relative to the oral, endo-tracheal anaesthesia tube for repositioning the oral, endo-tracheal anaesthesia tube and refixating the anaesthesia tube.

It is a feature of the present invention that the bandage according to the present invention for fixating an oral, endo-tracheal anaesthesia tube may be carried by the patient or person for an extended period of time without causing severe damage to the skin or the head of the person due to bed sores or other physical impact while providing a highly reliable fixation of the oral, endo-tracheal anaesthesia tube relative to the mouth of the patient or person and also relative to the trachea of the patient or person.

A particular advantage of the present invention relates to the fact that the bandage for fixating an oral, endo-tracheal anaesthesia tube may be produced from low cost materials providing, as compared to the above mentioned prior art fixation devices, a low cost device for fixating the oral, endo-tracheal anaesthesia tube relative to the mouth of a patient or person.

The above objects, the above features and the above advantages together with numerous other objects, features and advantages which will be evident from the below detailed description of preferred embodiments of the bandage according to the present invention are in accordance with the first aspect of the present invention obtained by means of a bandage for fixating an oral, endo-tracheal anaesthesia tube relative to the mouth of a person, comprising:

a support sheet of a flexible, substantially non-ductile material defining opposite side surfaces and defining contiguous first and second parts, the first part being provided with a coating, at one side surface thereof, of a first adhesive exhibiting the ability of adhering to the skin of a person, and being configurated so as to allow the first part to be adhered to the cheek of the person adjacent the mouth of the person leaving the mouth unobstructed, and the second part being provided with a coating, at one side surface thereof, of a second adhesive exhibiting the ability of adhering to the endo-tracheal anaesthesia tube, and being configured so as to allow the second part to be adhered to a segment of the tube extending outwardly from the mouth of the person.

According to the basic realization of the present invention, a bandage is provided which bandage comprises a support sheet which has on the one hand to be flexible in order to allow the support sheet to accomodate the physical shape of the head of the person to whom the bandage is applied, and on the other hand has to be of substantially non-ductile material which means that the support sheet should to only a reduced extent or to substantially no extent be elongated after the bandage has been applied in order to guarantee that the intentional and correct position of the oral, endo-tracheal anaesthesia tube relative to the mouth is maintained after the bandage has been applied. In order to provide the intentional and correct positioning and also fixation of the oral, endo-tracheal anaesthesia tube relative to the mouth of the person and also relative to the trachea of the person, the support sheet of the bandage comprises two parts which are, firstly, configured so as to allow the part in question to adhere to the intentional object either the cheek of the person or the segment of the tube extending outwardly from the mouth of the person and which, secondly, carry a respective adhesive which is selected taking into consideration the specific application as the adhesive of the first part has to adhere to the skin of the person whereas the adhesive of the second part has to adhere to the tube material and preferably allow a repositioning and refixation of the second part relative to the tube for altering or modifying the position of the oral, endo-tracheal anaesthesia tube relative to the mouth of the person and also relative to the trachea of the person. It is considered extremely important to obtain the repositioning and refixation capability as in most instances the oral, endo-tracheal anaesthesia tube has to be repositioned after the initial positioning and the fixation has been completed.

The bandage according to the present invention may be implemented in numerous configurations and employing different adhesives as will be described below. According to two alternative embodiments constituting a first and a second embodiment of the bandage according to the present invention, the first and second adhesives are applied to opposite side surfaces of the first and second parts, respectively, of the support sheet and applied to side surfaces of the second and first parts, respectively, of the support sheet constituting the same side surface of the support sheet, respectively. According to the first embodiment, the first and second adhesives are applied to opposite side surfaces and the support sheet is preferably provided with a through-going aperture at the transition between the first and second parts in order to allow that the first part may be fixated to the cheek of the person whereas the second part is adhered to the length of the tube extending outwardly from the mouth of the person. According to the presently preferred embodiment of the bandage according to the present invention, the first and second adhesives are applied to the same side surfaces of the support sheet which makes the method of producing the bandage far less complicated as compared to the method of producing a bandage having adhesives applied to opposite side surfaces.

In order to improve the adhesion of the first part to the skin of the person, the first part may advantageously be configured so as to at least partly encircle the mouth of the person in order to increase the area of adhesion as compared to a more simple embodiment in which the first part is adhered to the cheek of the person, exclusively.

In accordance with an advantageous embodiment of the bandage according to the present invention, the bandage constitutes a unitary structure and the first part encircles at least partly the second part. For providing the bandage as a unitary structure, the process of applying the bandage involves the process of applying only a single element.

According to an alternative embodiment of the bandage according to the present invention, the bandage comprises two elements to be assembled into a bandage and having respective parts together defining the first and second part. The bandage may further alternatively comprise more than two elements to be assembled into the bandage. By providing the bandage as a structure comprising two or more elements to be assembled during the process of applying the bandage, the elements may be positioned individually which in some instances simplifies the process of applying the bandage as compared to the process of applying a bandage constituting a unitary structure.

The two adhesives constituting the first and the second adhesives applied to the first and second parts of the support sheet of the bandage according to the present invention, may be applied to respective areas constituting the first and second part, respectively, in a single or a two-step adhesive application process. Alternatively, the first or the second part may be produced by positioning as additional sheet on the support sheet covering a part of the support sheet and including the alternative adhesive as compared to the adhesive which is applied in a continuous coating on the support sheet. Thus according to a first alternative embodiment, the third part is constituted by a composite structure including the material of the support sheet on which a second adhesive is provided, and a further foil of a flexible, substantially non-ductile material is adhered to the support sheet through the second adhesive and being provided with the first adhesive. According to an alternative embodiment, the second part is constituted by a composite structure including the material of the support sheet on which the first adhesive is provided, and a further foil of a flexible, substantially non-ductile material is adhered to the support sheet through the first adhesive and being provided with the second adhesive.

The first and the second adhesives provided at the first and the second part, respectively, of the support sheets, may be constituted by any appropriate adhesive fulfilling the purposes characteristic of the present invention. Advantageous adhesives are constituted by medical acrylic adhesives which have proven advantageous as on the one hand the adhesives exhibit excellent characteristics as to adhesion or fixation capability and on the other hand produce a minimum skin irritation effect. Alternatively, the adhesives may be constituted by medical rubber based adhesives which, however, may cause an increased allergic reaction as compared to the acrylic adhesives. The first and the second adhesives may, thus, be constituted by different or identical adhesives preferably of the above mentioned types.

The support sheet has to fulfil the above requirements as to flexibility and low ductility and has further in accordance with alternative applications to exhibit water repellant characteristics or alternatively water diffusion allowing capability. In case the bandage, according to the present invention, is used for surgical purposes, a water repellant material may be preferred in order to prevent the bandage from absorbing fluids during the surgery. Provided the bandage is used for long time hospitalization of the patient, the material of the support sheet is preferably a water diffusion allowing material in order to reduce the skin irritation effect as compared to a water non-diffusion allowing material. Examples of the above materials are foamed plastics materials or woven or non-woven fibrous materials such as polyethylene foam, woven or non-woven polyester foils or the like.

The above objects, the above features and the above advantages together with numerous other objects, features and advantages which will be evident from the below detailed description of preferred embodiments of the bandage according to the present invention are in accordance with the second aspect of the present invention obtained by means of an assembly for fixating an oral, endo-tracheal anaesthesia tube relative to the mouth of a person, comprising:

(i) a mouth piece to be positioned at the entry of the mouth of the person, at least partly encircling the endo-tracheal anaesthesia tube, and (ii) a bandage comprising:

a support sheet of a flexible, substantially non-ductile material defining opposite side surfaces and defining contiguous first and second parts, the first part being provided with a coating, at one side surface thereof, of a first adhesive exhibiting the ability of adhering to the skin of a person, and being configured so as to allow the first part to be adhered to the cheek of the person adjacent the mouth of the person leaving the mouth unobstructed, and the second part being provided with a coating, at one side surface thereof, of a second adhesive exhibiting the ability of adhering to the endo-tracheal anaesthesia tube, and being configured so as to allow the second part to be adhered to a segment of the tube extending outwardly from the mouth of the person and/or to a segment of the mouth piece extending outwardly from the mouth of the person.

The assembly according to the present invention comprises a mouth piece and further a bandage according to the first aspect of the present invention. The bandage of the assembly according to the second aspect of the present invention may preferably comprise any of the features of the bandage according to the first aspect of the present invention.

The mouth piece of the assembly according to the second aspect of the present invention may be implemented in numerous configurations fulfilling the main purpose of supporting the tube at the entry into the mouth of the person and the additional purpose of preventing the tube from being damaged in case the person sets his or her teeth. Thus, the mouth piece may comprise a tubular element which is threaded on the endo-tracheal anaesthesia tube or alternatively and preferably comprise a cylindrical wall element for receiving and at least partly encircling a segment of the endo-tracheal anaesthesia tube, and a flange element extending outwardly from the cylindrical wall element to a position in front of the lips of the mouth of the person. The cylindrical wall element, thus, is positioned in the mouth of the person and between the teeth of the person in order to mechanically support and protect the segment of the endo-tracheal anaesthesia tube which is received by the cylindrical wall element. The flange element is preferably fixated relative to the lips or at least one of the lips of the person as the bandage of the assembly is adhered to the flange element and to the adjacent part of the lip or lips of the patient or person.

The present invention will now be further described with reference to the drawing in which, FIG. 1b is a perspective and schematic view of the endo-tracheal anaesthesia tube fixated relative to the mouth of the patient or person my means of the first embodiment of the bandage according to the present invention shown in FIG. 1a.

FIG. 3b is a perspective and schematic view similar to the views of FIGS. 1b and 2b of the application of the third embodiment of the bandage according to the present invention shown in FIG. 3a, FIG. 4a is a schematic view similar to the views of FIGS. 1a, 2a and 3a of a fourth embodiment of the bandage according to the present invention, FIG. 5b is a perspective and schematic view of the endo-tracheal anaesthesia tube and the first embodiment of the mouth piece shown in FIG. 5a, FIG. 5c is a perspective and schematic view similar to the views of FIGS. 1b, 2b, 3b and 4b of the application of the fifth embodiment of the bandage shown in FIG. 5a and of the first embodiment of the mouth piece shown in FIGS. 5a and 5b.

FIG. 7b is a perspective and schematic view similar to the views of FIGS. 5c and 6c of the application of the third embodiment of the mouth piece and of the fourth embodiment of the bandage according to the present invention shown in FIG. 4a, FIG. 8 is a perspective and exploded view of the second embodiment of the bandage according to the present invention shown in FIGS. 2a and 2b disclosing the multilayer structure of the bandage.

Figure 1A:
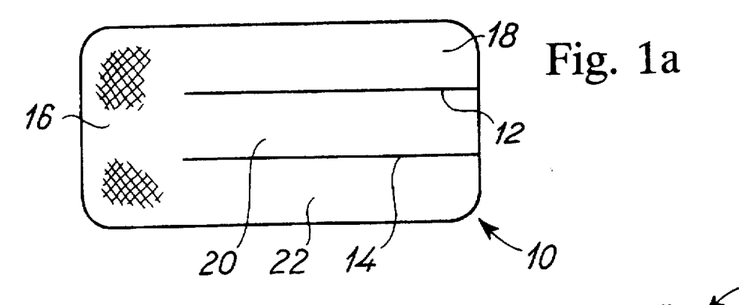
FIG. 1a is a schematic view of a first embodiment of a bandage for fixating an oral, endo-tracheal anaesthesia tube relative to the mouth of a patient or person.

In FIG. 1a, a first embodiment of the bandage is shown for fixating an oral, endo-tracheal anaesthesia tube relative to the mouth of a person. The bandage is designated the reference numeral 10 in its entirety and comprises a support sheet of a flexible, substantially non-ductile material such as a foil of a foamed plastics material, e.g. polyurethane foam, polyethylene foam or a woven or non-woven foil such as a non-woven foil made from fibers of polyester, polyamide, viscose or rayon or a combination thereof. The bandage 10 is of an overall rectangular configuration and is divided into a total of four contiguous segments as two lines of separation 12 and 14 extend from a short edge of the rectangular bandage. The two lines of separation define a major part 16 of the bandage and three elongated strips 18, 20 and 22.

At the side surface of the support sheet of the bandage opposite to the side surface disclosed in FIG. 1a, the support sheet is provided with adhesive coatings. According to the teachings of the present invention, the part 16 and the strips 18 and 22 are provided with an adhesive coating adapted to establish adhesion to the skin of the patient or person to whom the bandage is applied. Preferably, a medical acrylic adhesive is used for the adhesive coating of the segments 16, 18 and 22. The segment 20 constitutes a different part of the bandage which part is to be used for adhesion to the endo-tracheal anaesthesia tube. Consequently, the adhesive coating of the strip 20 preferably exhibits the ability of adhering to the material of the endo-tracheal anaesthesia tube and also of separating the strip from the endo-tracheal anaesthesia tube for repositioning or refixation of the strip relative to the tube. The entire bandage is as is well known in the art and as will be described below provided with a release paper, not shown in the drawing, which is removed prior to the application of the bandage.

Figure 1B:
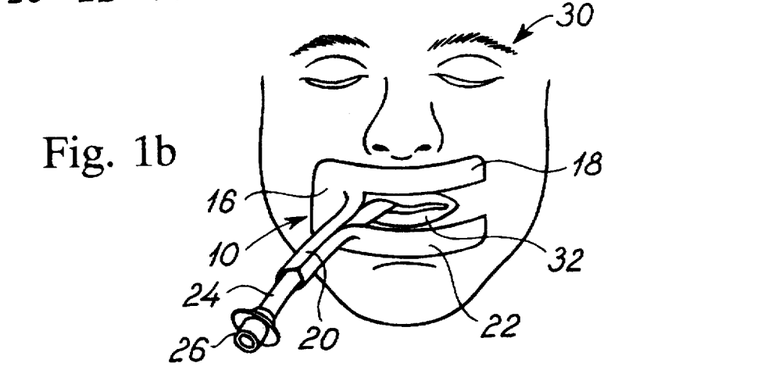

In FIG. 1b, the application of the bandage 10 is illustrated as an endo-tracheal anaesthesia tube 24 is introduced through the mouth of the patient or person. The head of the patient or person is designated the reference numeral 30 and the reference numeral 32 designates the lower lip of the head of the patient or person. The endo-tracheal anaesthesia tube is at its outer end provided with a fitting 26 for establishing a connection to external equipment as is well known in the art. The bandage 10 is applied partly encircling the mouth of the patient or person as the strip 18 is applied above the upper lip of the patient or person whereas the strip 22 is applied below the lower lip 32 of the patient or person. The part 16 is fixated to the right cheek of the head 30 of the patient or person as the junction between the part 16 and the strip 20 is positioned adjacent to the entry of the endo-tracheal anaesthesia tube 24 relative to the mouth of the patient or person. The strip 20 is in the application shown in FIG. 1b bent outwardly from the part 16 and the strips 18 and 22 and fixated to a length of the endo-tracheal anaesthesia tube 24 which length extends outwardly from the mouth of the patient or person.

Figure 2A:
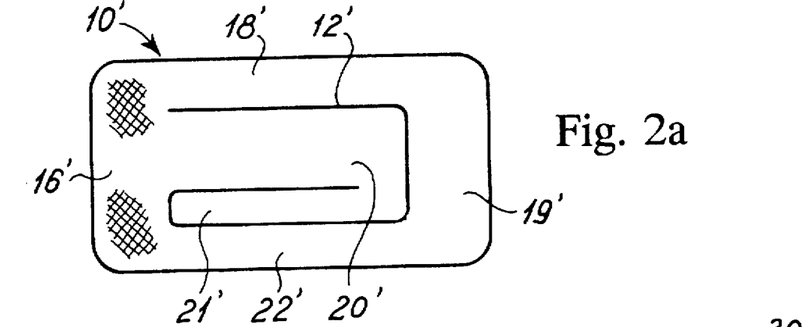
FIG. 2a is a schematic view similar to the view of FIG. 1a of a second embodiment of the bandage according to the present invention.

In FIG. 2a, a second embodiment 10' of the bandage according to the present invention is shown. In FIG. 2a, reference numerals are used adding the sign: ' identifying elements or components similar to the components of the first embodiment 10 described above with reference to FIG. 1a, however, indicated by the unmarked integer. The second embodiment 10' basically differs from the above described first embodiment 10 in that the line of separation 12' is of a tortuous configuration defining an inner part 20' which is further provided with an elongation 21'. The second embodiment 10' further differs from the above described first embodiment 10 in that the upper and lower strips 18' and 22' are interconnected through an additional part 19' establishing an outer annular part composed of the part 16', the upper and lower strips 18' and 22' and the part 19'.

Figure 2B:
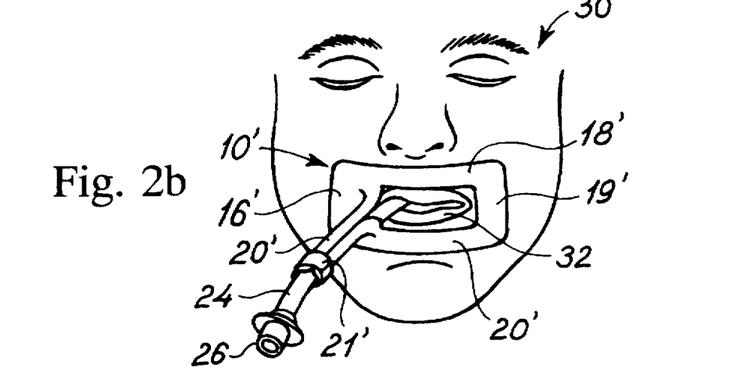
FIG. 2b is a perspective and schematic view similar to the view of FIG. 1b of the application of the second embodiment of the bandage according to the present invention shown in FIG. 2a, FIG. 3a is a schematic view similar to the views of FIGS. 1a and 2a of a third embodiment of the bandage according to the present invention.

In FIG. 2b, the application of the second embodiment 10' is shown. As is evident from FIG. 2b, the above described annular part encircles the mouth of the patient or person. The elongation 21' of the part 20' serves the purpose as is shown in FIG. 2b of sealing the outer end of the fixation of the part 20' relative to the endo-tracheal anaesthesia tube 24 as the elongation 21' is wound in overlapping relationship round the part 20' of the bandage 10'.

Figure 3A:
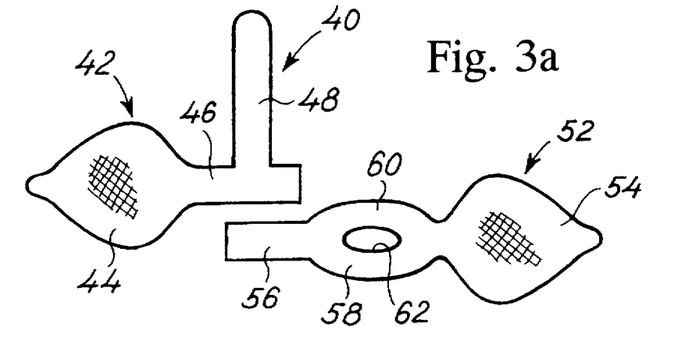

In FIG. 3a, a third embodiment of the bandage according to the present invention is shown designated the reference numeral 40 in its entirety. The bandage 40 differs from the above described first and second embodiments 10 and 10', respectively, described above with reference to FIGS. 1a and 2a, respectively, in that the bandage comprises two separate elements to be assembled into a structure at the stage of applying the bandage. Thus, the bandage 40 comprises two separate elements 42 and 52. Each of the elements 42 and 52 comprises a first part 44 and 54, respectively, to be applied to the cheek of a patient or person i.e. for adhering to the skin of the patient or person. From the first part 44, a strip 46 extends, and from the strip 46, a further strip 48 extends perpendicularly. The strip 46 basically serves the same purpose as the strip 20 of the first embodiment 10, whereas the strip 48 serves the same purpose as the elongation 21' of the part 20' of the second embodiment 10'.

From the first part 54 of the second element 52, the two curved strips 58 and 60 extend which strips are connected to a strip 56 and define an aperture 62. The first part 44 of the first element 42 and the first part 54 of the second element 52 are like the first parts 16 and 16' of the first and second embodiments 10 and 10' provided with an adhesive coating for adhering to the skin of the cheeks of the patient or person to whom the bandage 40 is fixated. The strips 46, 48, 56, 58 and 60 are contrary to the parts 44 and 54 provided with an adhesive coating similar to the strip 20 of the first embodiment 10, which adhesive coating allows the strips to be fixated and preferably released and refixated relative to the endo-tracheal anaesthesia tube which is introduced through the mouth of the patient or person as is shown in FIG. 3b.

Figures 3B, 4A:
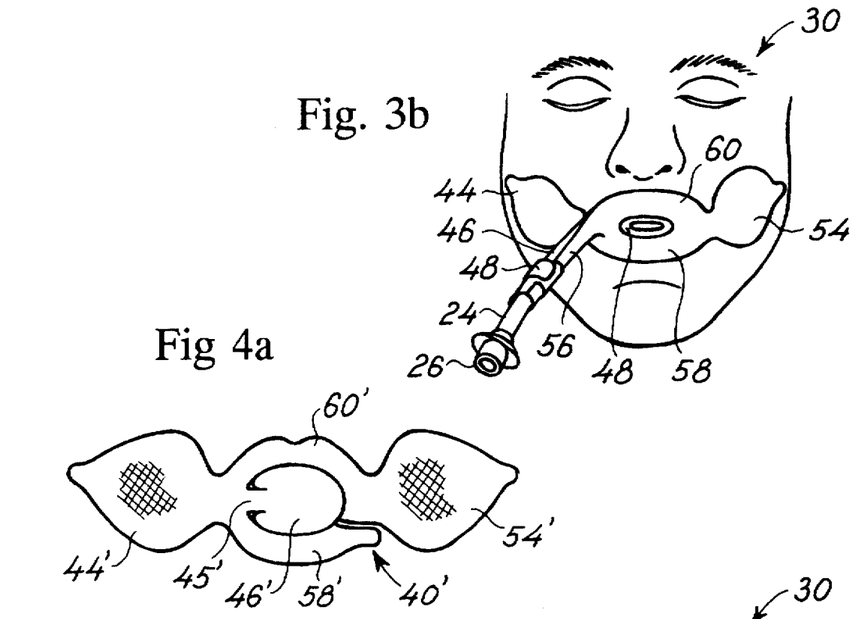

In FIG. 3b, the application of the two element embodiment or third embodiment 40 is shown. In FIG. 3b, a tongue arresting device or plug 48 is positioned between the lips and teeth of the patient or person serving the purpose of arresting the tongue in the intentional correct position within the mouth of the patient or person. The tongue arresting device 48 also ensures that the endo-tracheal anaesthesia tube 24 is not exposed to damage in case the patient or person sets his or her teeth during the anaesthesia treatment. Thus, the endo-tracheal anaesthesia tube 24 is positioned adjacent to the tongue arresting device. The tongue arresting device 48 is like the endo-tracheal anaesthesia tube 24 fixated by means of the bandage 44 as the curved strips 58 and 60 adhere to the tongue arresting plug 48 and also to the lips of the patient or person.

In FIG. 4a a fourth embodiment of the bandage according to the present invention is shown designated the reference numeral 40' in its entirety. The fourth embodiment 40' constitutes an embodiment reassembling the above described two element embodiment 40, however, combined into a single unitary structure. Thus, in FIG. 4a, elements or components similar to the above described elements or components of the third embodiment 40 are designated the same reference numerals, however adding the mark: '. Apart from constituting a unitary structure, the fourth embodiment 40' differs from the above described third embodiment 40 in that the part 46' serving the purpose of adhering to the endo-tracheal anaesthesia tube is concealed within the curved strips 58' and 60', however, ajoint to the strips 58 and 60' through a junction 45'. Contrary to the third embodiment 40, the curved strip 58' is also separated at one end thereof from the curved strip 60'.

Figure 4B:
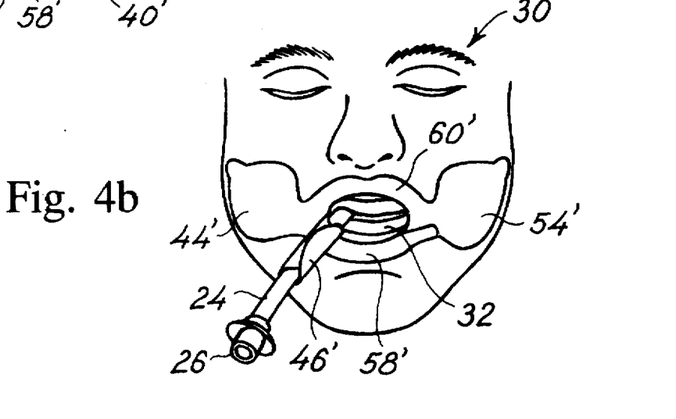
FIG. 4b is a perspective and schematic view similar to the views of FIGS. 1b, 2b and 3b of the application of the fourth embodiment of the bandage shown in FIG. 4a, FIG. 5a is a schematic view similar to the views of FIGS. 1a, 2a, 3a and 4a of a fifth embodiment of the bandage according to the present invention and of a first embodiment of the mouth piece to be used in connection with the bandage.

In FIG. 4b, the application of the fourth embodiment 40' of the bandage according to the present invention is shown, which application differs from the application of the above described third embodiment 40 shown in FIG. 3b in that the curved strips 58' and 60' leaves the lips of the patient or person 30 unobstructed.

Figures 5A, 5B, 5C:
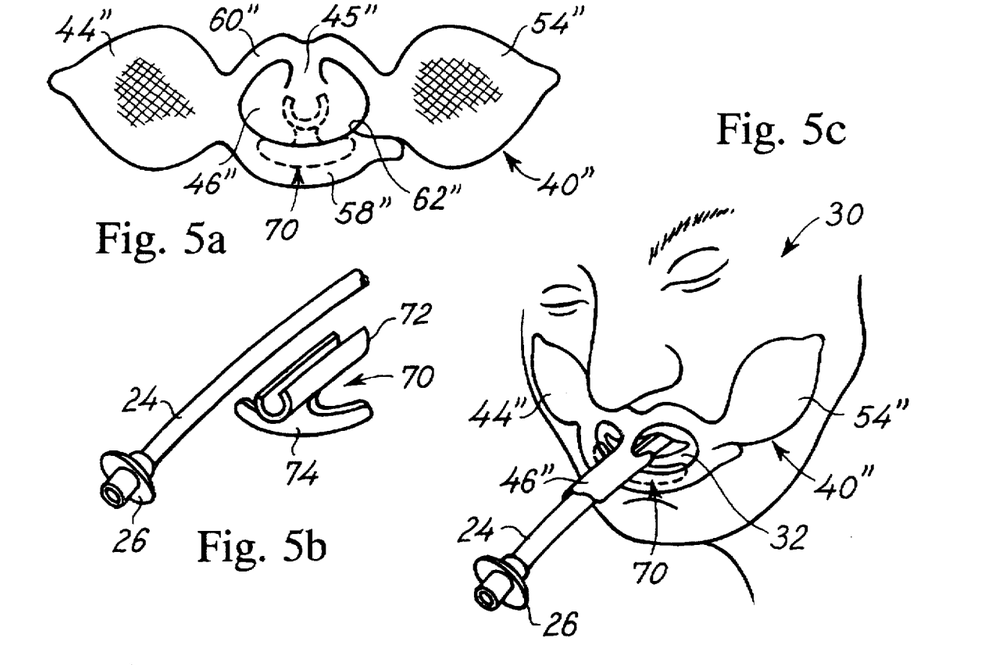

In FIG. 5a, a fifth embodiment of the bandage according to the present invention is shown designated by the reference numeral 40". In FIG. 5a, elements or components similar to or fulfilling the same purpose as the elements or components of the above described fourth embodiment 40' shown in FIG. 4a are designated the same reference numeral integer, however adding the additional mark: ". The fifth embodiment 40" basically differs from the above described fourth embodiment 40' in that the junction 45" through which the part 46" is connected to the curved strip 60" is positioned centrally relative to the overall structure and at the central part of the curved strip 60". In FIG. 5a, a first embodiment 70 of a mouth piece is also shown. The first embodiment 70 of the mouth piece is together with the endo-tracheal anaesthesia tube 24 disclosed in greater details in FIG. 5b.

The first embodiment 70 of the mouth piece comprises a cylindrical wall segment 72 from which a flange element 74 extends perpendicularly. The cylindrical wall element 72 serves the purpose of receiving and arresting a length of the endo-tracheal anaesthesia tube 24 whereas the flange element 74 is to be positioned outside the lips of the patient or person to whom the endo-tracheal anaesthesia tube 24 is applied and resting against the lower lip of the patient or person.

In FIG. 5c, the application of the fifth embodiment 40" of the bandage according to the present invention and the first embodiment 70 of the mouth piece is disclosed. As the flange element 74 of the mouth piece 70 is positioned in front of and resting against the lower lip 32 of the patient or person 30, a part of the cylindrical wall element 72 extends outwardly from the mouth of the patient or person. As the bandage 40" is applied circumferentially encircling the mouth of the patient or person as is shown in FIG. 5c, the part 46" of the bandage adheres to the outer protruding part of the cylindrical wall element 72 of the mouth piece 70 and also to a length of the endo-tracheal anaesthesia tube 24 for fixating and arresting the tube relative to the mouth piece 70.

Figures 6A, 6B, 6C:
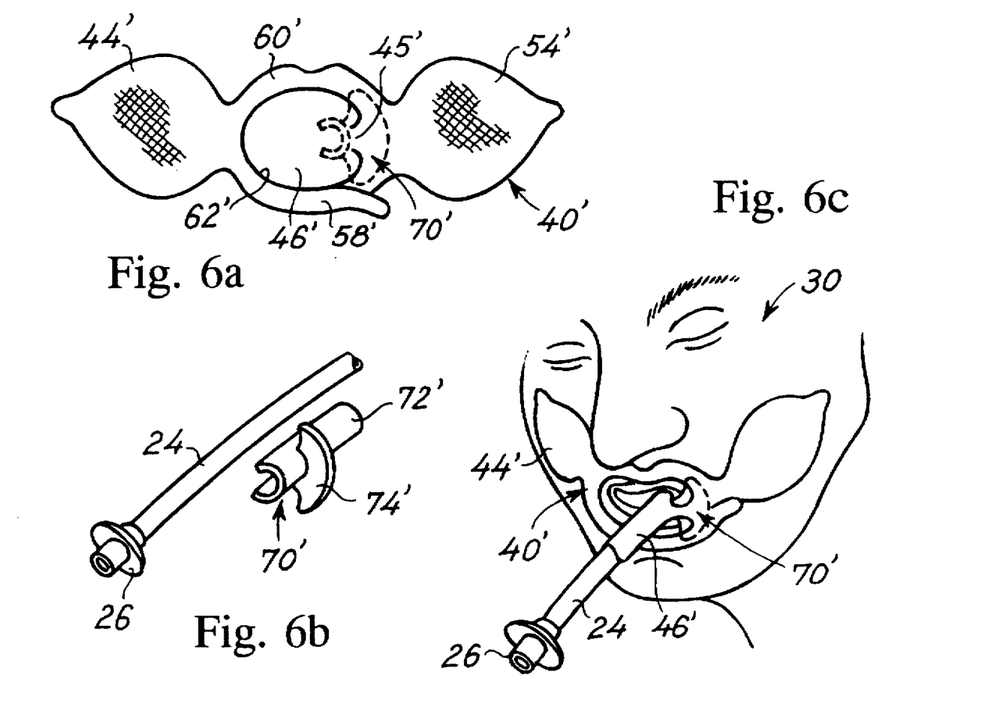
FIG. 6a is a perspective and schematic view similar to the views of FIGS. 1a, 2a, 3a, 4a and 5a of a second embodiment of the mouth piece and of the fourth embodiment of the bandage according to the present invention.
FIG. 6b is a perspective and schematic view similar to the view of FIG. 5b of the endo tracheal anaesthesia tube and of the second embodiment of the mouth piece.
FIG. 6c is a perspective and schematic view similar to the view of FIG. 5c of the application of the second embodiment of the mouth piece shown in FIGS. 6a and 6b and of the fourth embodiment of the bandage according to the present invention shown in FIG. 4a, FIG. 7a is a perspective and schematic view similar to the views of FIGS. 5b and 6b of a third embodiment of the mouth piece mounted on the endo-tracheal anaesthesia tube.

In FIG. 6a, a second embodiment 70' of the mouth piece is shown together with the above described fourth embodiment 40' of the bandage according to the present invention. The bandage 40' shown in FIG. 6a, constitutes a mirror image of the bandage 40' shown in FIG. 4a. The second embodiment 70' of the mouth piece differs from the above described first embodiment 70 in that the second embodiment is adapted to be positioned at the corner of the mouth contrary to the above described first embodiment 70 which is positioned centrally relative to the lower lip 32.

In FIG. 6b, the second embodiment 70' is shown in greater details comprising a cylindrical wall element 72' and a flange element 74' corresponding to the above described cylindrical wall element 72 and flange element 74, respectively, of the first embodiment 70 of the mouth piece.

In FIG. 6c, the application of the third embodiment 40' of the bandage according to the present invention and the second embodiment of the mouth piece 70' is illustrated disclosing the arresting and fixation of the mouth piece 70' at the corner of the mouth of the patient or person through the bandage 40" and, similar to the application of the first embodiment 70 of the mouth piece shown in FIG. 5c, the arresting of the mouth piece and also the endo-tracheal anaesthesia tube 24 by means of the part 46' of the bandage 40'.

Figures 7A, 7B:
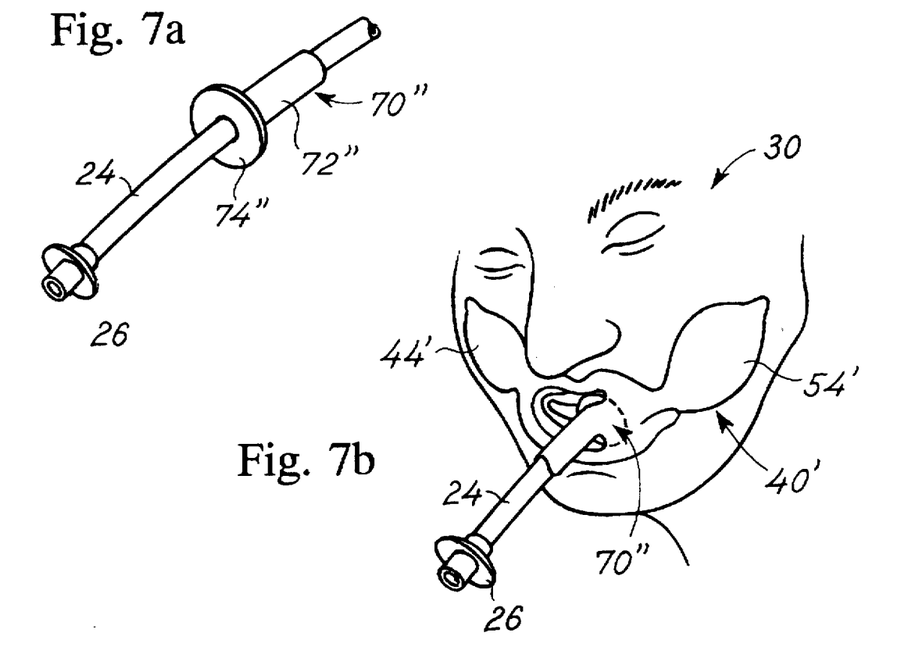

In FIG. 7a, a third embodiment 70" of the mouth piece is shown treaded on the endo-tracheal anaesthesia tube 24. The third embodiment 70" comprises a length of a tubular element 72" and an annular flange element 74" which is integrally connected to the tubular element 72" at one end thereof.

In FIG. 7b, the application of the third embodiment 70" is illustrated which application reassembles the application of the second embodiment 70' disclosed in FIG. 6c.

Figure 8:
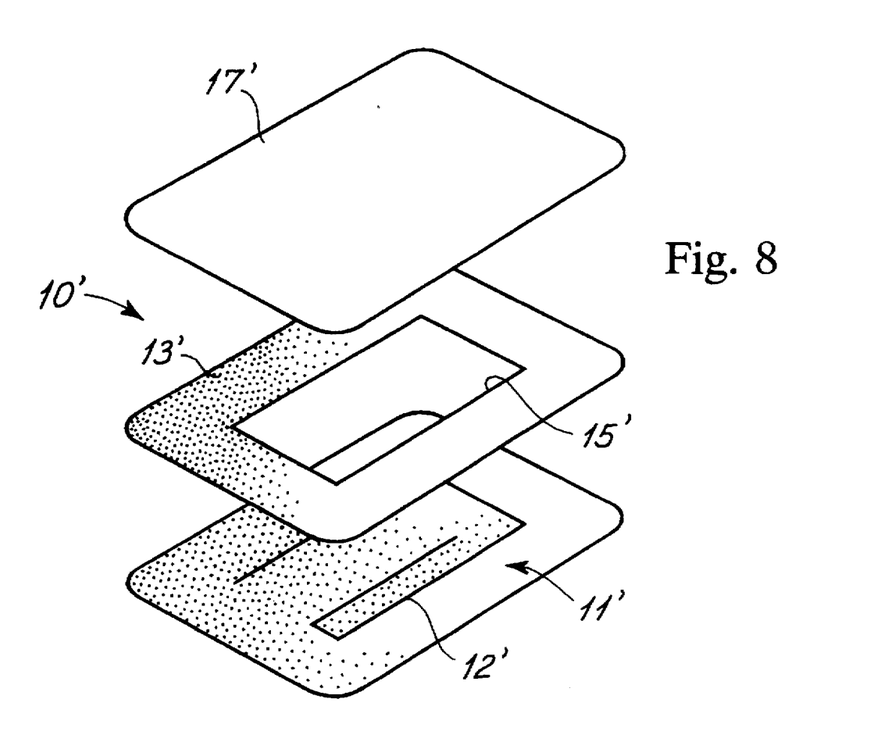

The above described embodiments of the bandage according to the present invention exhibit the characteristic feature of comprising a support sheet of a flexible, substantially non ductile material defining two parts, one of which is provided with an adhesive for adhering to the skin of the cheek of the patient or person to whom the bandage is applied, and another one of which is provided with an adhesive exhibiting the ability of adhering to the endo-tracheal anaesthesia tube and preferably allowing a separation of the part from the tube and refixation of the part relative to the tube. The first and second parts of the bandage according to the present invention may be produced by applying the relevant adhesives at respective parts of the support sheet for producing the first and second parts of the bandage. Alternatively, the bandage may be produced as mentioned above as a composite structure from two or more sheets. In FIG. 8, the second embodiment 10' of the bandage according to the present invention is shown in exploded view disclosing a first sheet 11' in which the tortously formed separation line 12' is produced and on top of which an annular sheet 13' is positioned as the annular sheet 13' is provided with a central aperture 15' exposing the central part 20' and the elongation 21' of the sheet 11'. The sheet 13' is adhered to the sheet 11' through the adhesive coating also covering the central part of the sheet 11' which part is intended to adhere to the endo-tracheal anaesthesia tube 24 as described above with reference to FIG. 2b. The annular sheet 13' is provided with an adhesive coating of the above described medical type providing a strong adhesion to the skin of the person to whom the bandage is applied. In FIG. 8, the reference numeral 17' designates a release sheet which in accordance with a technique well known in the art is applied to the bandage for protecting the adhesive coatings of the sheets 11' and 13' from being contaminated by dust and dirt prior to use.

Figure 9:
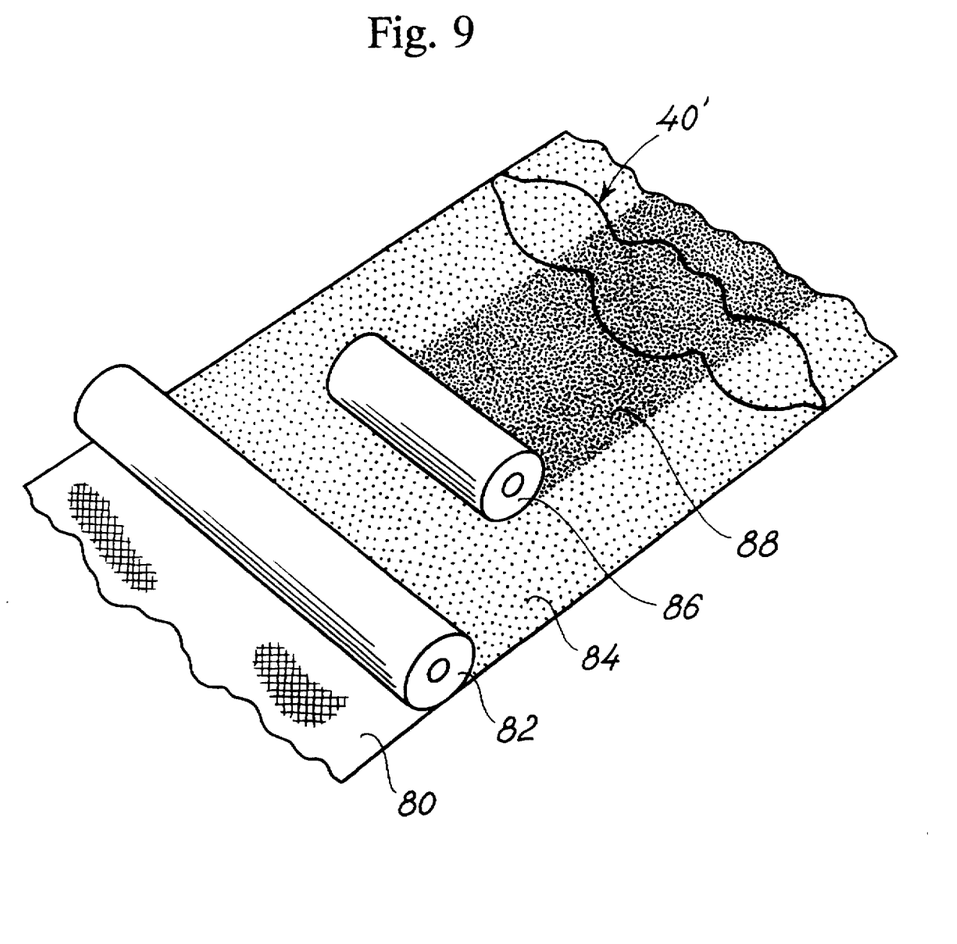
FIG. 9 is a perspective and schematic view of a method of producing the fourth embodiment of the bandage according to the present invention shown in FIGS. 4a, 4b, 6a, 6c and 7b and illustrating the multilayer structure of the bandage.

In FIG. 9, a different technique of producing a multilayer structure of the bandage is shown according to which technique the central area of the bandage constituting the third embodiment 40' is reinforced by a separate adhesive carrying foil. Thus, the reference numeral 80 designates a support sheet preferably of a flexible, substantial non-ductile materials such as the above described foam materials or the above described woven or non-woven fibrous materials. By means of a roller 82, an adhesive coating is applied to an upper side surface of he sheet 80 which adhesive coating is designated the reference numeral 84 and constitutes the strong skin bonding adhesive of the parts 44' and 54' of the fourth embodiment 40' of the bandage according to the present invention. By means of a further roller 86, a central part of the foil is applied with an additional layer of a reinforcing full on which a further adhesive is applied. The adhesive of the reinforcing foil is designated the reference numeral 88.

As is evident from FIG. 9, the reinforcing foil supporting the adhesive 88 covers those areas of the foil from which the curved strips 58' and 60' are produced and also the first part 46' and the junction 45'. Furthermore, the reinforcing foil covers the narrowing parts bridging the curved strips 58' and 60' and the parts 44' and 54' of the bandage. The reinforcing support foil, thus, reduces the ductility of the bandage at those parts of the bandage which are contacted with the endo-tracheal anaesthesia tube and which transfer the tensile forces from the endo-tracheal anaesthesia tube to the foil of the bandage.

I claim:

1. A bandage for fixating an oral, endo-tracheal anaesthesia tube relative to a mouth of a person, comprising:

a support sheet of a flexible, substantially non-ductile material defining opposite side surfaces and defining contiguous first and second parts, said first part being provided with a coating, at one side surface thereof, of a first adhesive exhibiting an ability of adhering to a skin of said person, and being configured so as to allow said first part to be adhered to a cheek of said person adjacent said mouth of said person leaving said mouth unobstructed, and said second part being provided with a coating, at one side surface thereof, of a second adhesive exhibiting an ability of adhering to said endo-tracheal anaesthesia tube, and being configured so as to allow said second part to be adhered to a segment of said tube extending outwardly from said mouth of said person, wherein said bandage constitutes a unitary structure, and said first part at least partly encircles said second part.

2. The bandage according to claim 1, wherein said first and said second adhesives are applied to opposite side surfaces of said first and said second parts, respectively, of said support sheet.

3. The bandage according to claim 2, wherein said support sheet is provided with a through-going aperture at a transition between said first and said second parts.

4. The bandage according to claim 1, wherein said first and said second adhesives are applied to said surfaces of said second and said first parts, respectively, of said support sheet constituting the same side surface of said support sheet.

5. The bandage according to claim 1, wherein said first part is configured so as to at least partly encircle said mouth of said person.

6. The bandage according to claim 1, wherein said bandage comprises two elements to be assembled into said bandage and having respective parts together defining said first and said second parts.

7. The bandage according to claim 1, wherein said first part is constituted by a composite structure including said material of said support sheet on which said second adhesive is provided, and a foil of a flexible, substantially non-ductile material adhering to said support sheet through said second adhesive and provided with said first adhesive.

8. The bandage according to claim 1, wherein said second part is constituted by a composite structure including said material of said support sheet on which said first adhesive is provided, and a foil of a flexible, substantially non-ductile material adhering to said support sheet through said first adhesive and provided with said second adhesive.

9. The bandage according to claim 1, wherein said first and said second adhesives are constituted by medical adhesives such as acrylic adhesives.

10. The bandage according to claim 1, wherein said support sheet is made from one of a water repellant material and a water diffusion-allowing material.

11. The bandage according to claim 2, wherein said first part is configured so as to at least partly encircle said mouth of said person.

12. The bandage according to claim 3, wherein said first part is configured so as to at least partly encircle said mouth of said person.

13. The bandage according to claim 4, wherein said first part is configured so as to at least partly encircle said mouth of said person.

14. The bandage according to claim 2, wherein said bandage comprises two elements to be assembled into said bandage and having respective parts together defining said first and said second parts.

15. The bandage according to claim 3, wherein said bandage comprises two elements to be assembled into said bandage and having respective parts together defining said first and said second parts.

16. The bandage according to claim 4, wherein said bandage comprises two elements to be assembled into said bandage and having respective parts together defining said first and said second parts.

17. The bandage according to claim 5, wherein said bandage comprises two elements to be assembled into said bandage and having respective parts together defining said first and said second parts.

18. The bandage according to claim 2, wherein said first part is constituted by a composite structure including said material of said support sheet on which said second adhesive is provided, and a foil of a flexible, substantially non-ductile material adhering to said support sheet through said second adhesive and provided with said first adhesive.

19. The bandage according to claim 3, wherein said first part is constituted by a composite structure including said material of said support sheet on which said second adhesive is provided, and a foil of a flexible, substantially non-ductile material adhering to said support sheet through said second adhesive and provided with said first adhesive.

20. The bandage according to claim 4, wherein said first part is constituted by a composite structure including said material of said support sheet on which said second adhesive is provided, and a foil of a flexible, substantially non-ductile material adhering to said support sheet through said second adhesive and provided with said first adhesive.

21. The bandage according to claim 5, wherein said first part is constituted by a composite structure including said material of said support sheet on which said second adhesive is provided, and a foil of a flexible, substantially non-ductile material adhering to said support sheet through said second adhesive and provided with said first adhesive.

22. The bandage according to claim 6, wherein said first part is constituted by a composite structure including said material of said support sheet on which said second adhesive is provided, and a foil of a flexible, substantially non-ductile material adhering to said support sheet through said second adhesive and provided with said first adhesive.

23. The bandage according to claim 2, wherein said second part is constituted by a composite structure including said material of said support sheet on which said first adhesive is provided, and a foil of a flexible, substantially non-ductile material adhering to said support sheet through said first adhesive and provided with said second adhesive.

24. The bandage according to claim 3, wherein said second part is constituted by a composite structure including said material of said support sheet on which said first adhesive is provided, and a foil of a flexible, substantially non-ductile material adhering to said support sheet through said first adhesive and provided with said second adhesive.

25. The bandage according to claim 4, wherein said second part is constituted by a composite structure including said material of said support sheet on which said first adhesive is provided, and a foil of a flexible, substantially non-ductile material adhering to said support sheet through said first adhesive and provided with said second adhesive.

26. The bandage according to claim 5, wherein said second part is constituted by a composite structure including said material of said support sheet on which said first adhesive is provided, and a foil of a flexible, substantially non-ductile material adhering to said support sheet through said first adhesive and provided with said second adhesive.

27. The bandage according to claim 6, wherein said second part is constituted by a composite structure including said material of said support sheet on which said first adhesive is provided, and a foil of a flexible, substantially non-ductile material adhering to said support sheet through said first adhesive and provided with said second adhesive.

28. The bandage according to claim 2, wherein said first and said second adhesives are constituted by medical adhesives such as acrylic adhesives.

29. The bandage according to claim 3, wherein said first and said second adhesives are constituted by medical adhesives such as acrylic adhesives.

30. The bandage according to claim 4, wherein said first and said second adhesives are constituted by medical adhesives such as acrylic adhesives.

31. The bandage according to claim 5, wherein said first and said second adhesives are constituted by medical adhesives such as acrylic adhesives.

32. The bandage according to claim 6, wherein said first and said second adhesives are constituted by medical adhesives such as acrylic adhesives.

33. The bandage according to claim 7, wherein said first and said second adhesives are constituted by medical adhesives such as acrylic adhesives.

34. The bandage according to claim 8, wherein said first and said second adhesives are constituted by medical adhesives such as acrylic adhesives.

35. The bandage according to claim 2, wherein said support sheet is made from one of a water repellent material and a water diffusion-allowing material.

36. The bandage according to claim 3, wherein said support sheet is made from one of a water repellent material and a water diffusion-allowing material.

37. The bandage according to claim 4, wherein said support sheet is made from one of a water repellent material and a water diffusion-allowing material.

38. The bandage according to claim 5, wherein said support sheet is made from one of a water repellent material and a water diffusion-allowing material.

39. The bandage according to claim 6, wherein said support sheet is made from one of a water repellent material and a water diffusion-allowing material.

40. The bandage according to claim 7, wherein said support sheet is made from one of a water repellent material and a water diffusion-allowing material.

41. The bandage according to claim 8, wherein said support sheet is made from one of a water repellent material and a water diffusion-allowing material.

42. The bandage according to claim 9, wherein said support sheet is made from one of a water repellent material and a water diffusion-allowing material.

43. An assembly for fixating of an oral, endo-tracheal anaesthesia tube relative to a mouth of a person, comprising:
   (i) a mouth piece to be positioned at an entry of said mouth of said person, at least partly encircling said endo-tracheal anaesthesia tube, and
   (ii) a bandage comprising:
      a supporting sheet of flexible, substantially non-ductile material defining opposite said surfaces and defining contiguous first and second parts,
      said first part provided with a coating, at one side surface thereof, of a first adhesive exhibiting an ability of adhering to a skin of said person, and configured so as to allow said first part to be adhered to a cheek of said person adjacent said mouth of said person leaving said mouth unobstructed, and
      said second part provided with a coating, at one side surface thereof, of a second adhesive exhibiting an ability of adhering to said endo-tracheal anaesthesia tube, and configured so as to allow said second part to be adhered to at least one of a segment of said endo-tracheal anaesthesia tube extending outwardly from said mouth of said person and a segment of said mouth piece extending outwardly from said mouth of said person.

44. The assembly according to claim 43, wherein:
said first and said second adhesives are applied to opposite side surfaces of said first and said second parts, respectively, of said support sheet.

45. The assembly according to claim 43, wherein said mouth piece comprises:
a cylindrical wall element for receiving and at least partly encircling a segment of said endo-tracheal anaesthesia tube, and
a flange element extending outwardly from said cylindrical wall element to be positioned in front of lips of said mouth of said person.

46. The assembly according to claim 43, wherein:
said support sheet is provided with a through-going aperture at a transition between said first and said second parts.

47. The assembly according to claim 43, wherein:
said first and said second adhesives are applied to side surfaces of said second and said first parts, respectively, of said support sheet constituting the same side surface of said support sheet.

48. The assembly according to claim 43, wherein:
said first part is configured so as to at least partly encircle said mouth of said person.

49. The assembly according to claim 43, wherein:
said bandage of said assembly constitutes a unitary structure, and said first part at least partly encircles said second part.

50. The assembly according to claim 43, wherein:
said bandage comprises two elements to be assembled into said bandage and having respective parts together defining said first and said second parts.

51. The assembly according to claim 43, wherein:
said first part is constituted by a composite structure including said material of said support sheet on which said second adhesive is provided, and a foil of a flexible, substantially non-ductile material adhering to said support sheet through said second adhesive and provided with said first adhesive.

52. The assembly according to claim 43, wherein:
said second part is constituted by a composite structure including said material of said support sheet on which said first adhesive is provided, and a foil of a flexible, substantially non-ductile material adhering to said support sheet through said first adhesive and provided with said second adhesive.

53. The assembly according to claim 43, wherein:
said first and said second adhesives are constituted by medical adhesives such as acrylic adhesives.

54. The assembly according to claim 43, wherein:
said support sheet is made from one of a water repellant material and a water diffusion-allowing material.

55. The assembly according to claim 44, wherein said mouth piece comprises:
a cylindrical wall element for receiving and at least partly encircling a segment of said endo-tracheal anaesthesia tube, and
a flange element extending outwardly from said cylindrical wall element to be positioned in front of lips of said mouth of said person.

56. The bandage according to claim 10, wherein said support sheet is made from one of a foamed plastics material, a woven fiber material, and a non-woven fiber material.

57. The bandage according to claim 10, wherein said support sheet is made from one of a polyethylene foam, a woven polyester foil, and a non-woven polyester foil.

* * * * *